United States Patent [19]

Seeler

[11] Patent Number: 4,617,921
[45] Date of Patent: Oct. 21, 1986

[54] THERMALLY ACTUATED IMMOBILIZING STRUCTURE

[76] Inventor: C. Oliver Seeler, P.O. Box 246, Albion, Calif. 95410

[21] Appl. No.: 694,877

[22] Filed: Jan. 25, 1985

[51] Int. Cl.[4] .............................................. A61F 5/04
[52] U.S. Cl. ............................... 128/89 R; 128/87 R; 128/90
[58] Field of Search .................... 128/89 R, 89 A, 90, 128/87 R, 133–134

[56] References Cited

U.S. PATENT DOCUMENTS

| Re. 27,957 | 4/1974 | Larson | 128/89 |
|---|---|---|---|
| 974,294 | 11/1910 | Pond | 128/89 R |
| 2,802,463 | 8/1957 | Simjian | 128/87 |
| 2,933,083 | 4/1960 | Kozdas | 128/89 R |
| 3,110,307 | 11/1963 | Hamilton | 128/89 |
| 3,212,497 | 10/1965 | Dickinson | 128/87 |
| 3,643,656 | 2/1972 | Young et al. | 128/90 |
| 3,701,349 | 10/1972 | Larson | 128/89 R |
| 3,745,998 | 7/1978 | Rose | 128/89 R |
| 3,762,404 | 10/1973 | Sakita | 128/89 |
| 3,993,219 | 12/1976 | Mercer et al. | 128/89 R |
| 4,039,039 | 8/1977 | Gottfried | 128/87 R |
| 4,161,175 | 7/1979 | Bentele | 128/89 R |
| 4,261,349 | 4/1981 | Lambson et al. | 128/89 R |
| 4,300,542 | 11/1981 | Baron | 128/87 R |
| 4,508,112 | 4/1985 | Seeler | 128/89 R |

OTHER PUBLICATIONS

Machinery's Handbook, 20th ed., p. 2270, "Melting Points of Alloys of Low Fusing Point".

Primary Examiner—Gene Mancene
Assistant Examiner—C. W. Shedd
Attorney, Agent, or Firm—Townsend and Townsend

[57] ABSTRACT

The present invention is directed to a thermally actuated immobilizing structure useful as a splint, as a cast and for immobilizing, positioning, grasping or manipulating inanimate objects. The structure includes a flexible container containing a thermoplastic material and a matrix material embedded in the thermoplastic material. The matrix material preferably comprises elongate, generally parallel strands. The thermoplastic material and the strands are adapted to permit relatively unhindered relative movement among the strands when the thermoplastic material is flowable so the structure can be formed into the desired shape. The thermoplastic material and the strands are adapted to substantially inhibit or prevent relative movement among the strands to lock the strands in place, thus forming a rigid structure, when the thermoplastic material is solid. The strands preferably have roughened surfaces so adjacent strands are mechanically interlocked to inhibit relative longitudinal movement among the strands.

27 Claims, 11 Drawing Figures

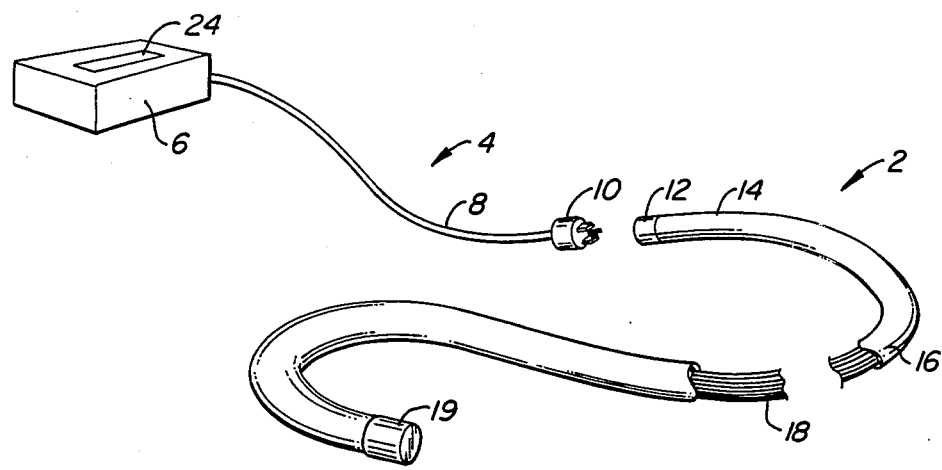
FIG._1.
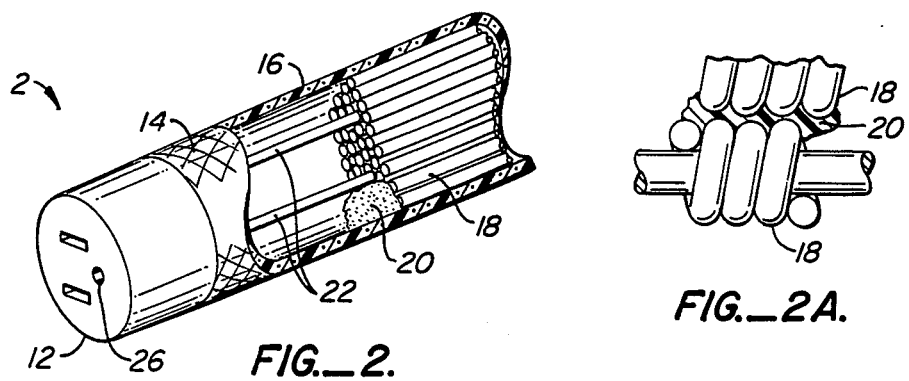
FIG._2.  FIG._2A.
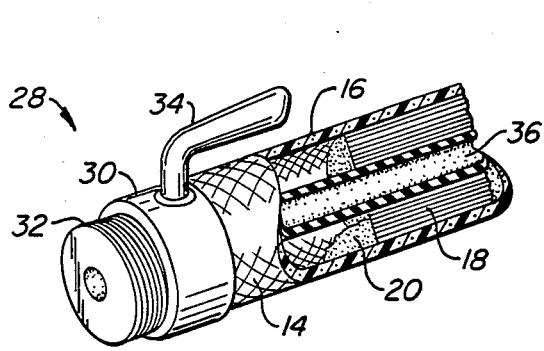
FIG._3.
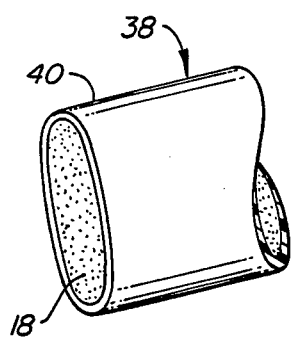
FIG._4.

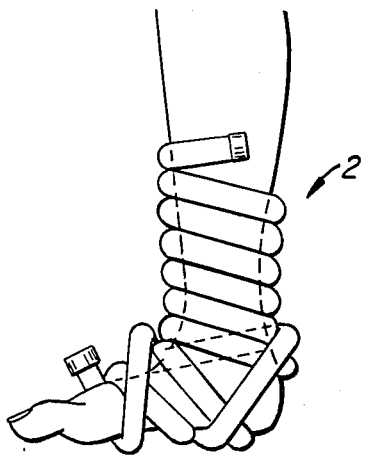
FIG._5.
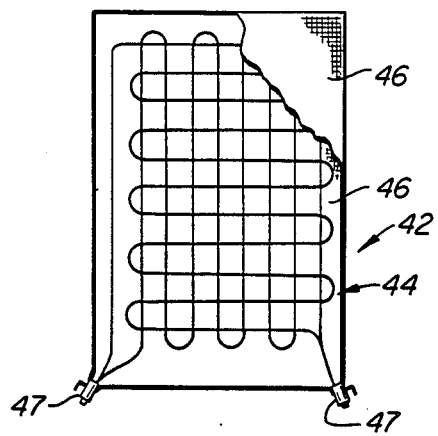
FIG._6.
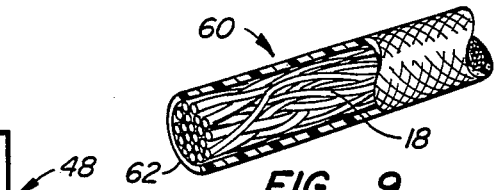
FIG._9.
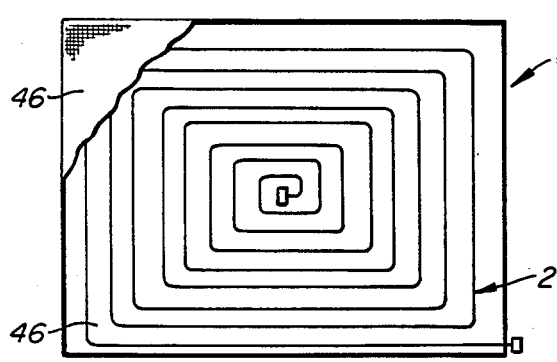
FIG._7.
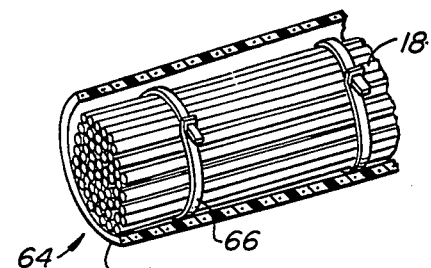
FIG._10.
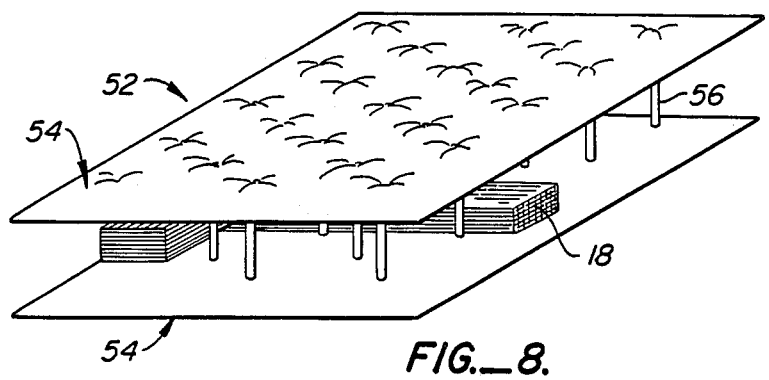
FIG._8.

THERMALLY ACTUATED IMMOBILIZING STRUCTURE

BACKGROUND OF THE INVENTION

Accident victims who have sustained serious injury usually must be transported to a medical facility to receive appropriate treatment. However, many injuries can be made worse if the victim is moved improperly. Therefore before moving an accident victim one usually attempts to immobilize the injured body parts. This is often done using various types of rigid splints pressed against the body with straps or other restraining devices. For example, see U.S. Pat. No. 4,211,218 to Kendrick. This patent shows a jacket-like device used to support the head, neck and back so the accident victim can be moved while restraining spinal movement. However, such immobilizing devices can be somewhat difficult to place on an accident victim without gross movements of the victim. Further, standard splint-type restraining devices using straps tend to squeeze the victim's body to in effect use the body as a structural element adding rigidity to the combination of the restraining device and the body part. This can cause further complications depending upon the type and extent of injury. Also, splints are often configured for use with specific body parts so many types must be carried by emergency first aid crews.

Another structure which could be used as a temporary splint is shown in U.S. Pat. No. 3,212,497 to Dickinson. This type of temporary splint uses a nonporous outer bag and a porous inner bag containing a mass of discrete particles. After being fitted to the injured body part, the outer bag is evacuated to allow the external atmospheric pressure to force the discrete particles against one another to form a rigid mass. The temporary splint is thus locked into the configuration, such as surrounding a patient's arm, it was in before the vacuum was applied to the outer bag. Although this type of temporary splint can be used with different body parts, it may tend to squeeze the patient when the vacuum is drawn. Also, the maximum pressure available for rigidifying the mass of discrete particles is atmospheric pressure; therefore such a splint may not be suitable when significant structural support is needed, such as when supporting an accident victim's head, neck and back. Also, vacuum actuated splints require the use of a vacuum pump, which are often not readily available.

Therefore, what has been missing in the prior art is a temporary splint which can be used to immobilize different body parts and which is strong enough to immobilize a patient's head, neck and back without squeezing the patient.

SUMMARY OF THE INVENTION

The present invention is directed to a thermally actuated immobilizing structure finding particular utility as an emergency splint, as a therapeutic cast and as a structure for immobilizing or engaging inanimate objects. The structure includes a flexible container containing a thermoplastic material and a matrix material embedded in the thermoplastic material. The matrix material preferably comprises elongate, generally parallel strands. The thermoplastic material and the strands are adapted to permit relatively unhindered relative movement among the matrix elements when the thermoplastic material is flowable so the structure can be formed about an object or a body part to be immobilized. The thermoplastic material and the matrix material are adapted to substantially inhibit or prevent relative movement among the matrix elements to lock the matrix material in place, thus forming a rigid structure, when the thermoplastic material is solid.

Various sources of heat can be used to heat the thermoplastic material. These sources include external heating of the structure by conduction, convection or radiation. The structure can also be heated externally by induction, such as by using microwaves, magnetic fields and so forth. Electric heating elements may be incorporated within the immobilizing structure, either directly among the matrix elements or incorporated into the container. If the matrix elements are elongate metal strands, electricity may be passed directly through the matrix material to heat the thermoplastic material. Chemical heating means may also be resorted to.

Typically, after the thermoplastic material is heated, allowing the immobilizing structure to be formed into its desired shape, cooling may take place unassisted. In certain circumstances it may be desired to augment cooling to speed the rate of cooling, such as when the ambient temperature is high. Also, in certain circumstances, the thermoplastic material will be liquid at ambient temperatures and must be cooled for rigidification; although not anticipated to be commonly used, this configuration is also contemplated. The assisted cooling can be accomplished externally or internally. For example, cooling can be assisted by blowing cool air across the surface of the structure or by immersing the immobilizing structure and the restrained object in a cool water bath. Also, the immobilizing structure may incorporate a fluid conduit adaptable for passing heated and cooled fluids through it.

The thermoplastic material will, in most cases, have a low melting point somewhat higher than the expected ambient temperature at which the immobilizing structure is to be used. In some applications, such as with emergency or therapeutic casts, it is important that the thermoplastic material have a relatively low melting temperature to avoid overheating the body part being immobilized. When used as a cast it may be desired to use the immobilizing structure in conjunction with a thermally insulating pad to protect the person's skin from overheating and yet allow the immobilizing structure to cool at a reasonable rate. In other applications, such as when temporarily positioning steel machine members so the item being immobilized is not heat sensitive, a higher melting point thermoplastic material can be used. This allows a wider choice of thermoplastic materials.

The elongate strands preferably have surfaces which are not smooth. Thus, when the strands are adjacent one another, relative longitudinal movement of the strands can occur only when some degree of lateral shifting of adjacent strands, due to high points on the surface of one strand fitting within surface depressions of adjacent strands, takes place.

The thermoplastic material acts to fill in the space between the matrix elements. Once the thermoplastic material hardens, the closely spaced, typically longitudinally mechanically interlocked, matrix elements must shift laterally and thus compress the thermoplastic material before sliding longitudinally relative to one another. Therefore, the thermoplastic material should have reasonable compression strength to hinder this movement.

The matrix elements sustain most of the load. However, the thermoplastic material is preferably not excessively brittle. The thermoplastic material should also not degrade with repeated melting, and should not be reactive with the container nor with the matrix elements. The electric properties of the thermoplastic material may be pertinent if heating is to be accomplished by induction or microwave. Thermal conductivity of the thermoplastic material is also important whenever the structure is heated locally, such as by internal electrical resistance heaters or by external heating.

The container must be flexible, but should be resistant to localized general swelling or bulging. This is important because it is necessary to keep the matrix elements closely grouped when the thermoplastic material is flowable.

The elongate strands constituting the matrix material have been described as being generally parallel. They may be parallel or they may be woven, twisted or braided in a manner similar to wire rope. The phrase generally parallel is intended to cover these and similar arrangements.

If the elongate strands are woven or braided, the strands, rather than the container housing them, would tend to keep themselves in close physical contact. This would eliminate or reduce the need for the container to keep the strands in physical contact. In such case the container could be used mainly to keep the thermoplastic material from being lost when melted. In some cases the thermoplastic material may naturally stay within the interstices among the strands even when flowable. This may be due, for example, to the affinity between the thermoplastic material and the strands or be due to the use of a thermoplastic material which is very viscous when heated to a flowable condition, or both. In such a situation an outer container may be eliminated.

Another feature of the invention is the use of a tubular container, which can be either round or flattened. This design allows a hose-like immobilizing structure to be used on a variety of body parts, rather than being specially adapted to, for example, the hand, forearm, or ankle. Thus excessive numbers of casts or temporary splints, each adapted for a specific body part, are not needed. Such an immobilizing structure is also well adapted for engaging various inanimate objects as well.

The present invention can be incorporated into a blanket-type mobilizing structure. In one blanket embodiment, one or more tubular immobilizing structures are arranged within a quilt or blanket-like structure. The tubes can be arranged in various patterns, such as a flat spiral, a flat random maze or a woven pattern using two sets of parallel tubes arranged transversely to one another. Such an immobilizing blanket can be used advantageously for placement around an accident victim requiring a large body area to be immobilized. After cooling, the immobilizing blanket will encase the victim in a conforming, rigid cocoon so that the body position can be maintained during transport to the hospital.

Another advantage of the invention is that the structure will remain rigid until the user takes an affirmative step to melt the thermoplastic material. The user merely needs to keep the thermoplastic material below its melting point to keep the structure rigid. Therefore there is little chance that the structure will inadvertently become flexible, such as exists with various pressure actuated immobilizing structures. It is thus particularly useful for both temporary or emergency situations as well as for longer term uses.

The invention has been described in terms of its use as a splint or cast. However, it is to be understood that the invention is also suitable for immobilizing, positioning, grasping or manipulating inanimate objects as well. For example, a tubular immobilizing structure may be used during underwater or outer space salvage operations to securely grasp unwieldy or otherwise hard-to-handle objects.

Other features and advantages of the invention will appear from the following description in which the preferred embodiments have been set forth in detail in conjunction with the accompanying drawings.

BRIEF DESCRIPTION OF THE DRAWINGS

FIG. 1 shows a tubular embodiment of the immobilizing structure of the invention connected to a source of electricity.

FIG. 2 is an enlarged isometric view of the connection end of the embodiment of FIG. 1.

FIG. 2A is an enlarged view of a section of two adjacent matrix wires with thermoplastic material between them.

FIG. 3 is an isometric view of one end of an alternative embodiment of the immobilizing structure of FIG. 1.

FIG. 4 is a cross-sectional isometric view of a flattened tubular embodiment of the invention.

FIG. 5 shows the embodiment of FIG. 1 wrapped around a person's lower leg and ankle.

FIG. 6 is a simplified plan view showing a blanket embodiment of the invention incorporating a tubular embodiment similar to that of FIG. 3 in a woven pattern.

FIG. 7 is a simplified plan view of a second blanket embodiment with the tubular immobilizing structure of FIG. 1 wound in a flat spiral.

FIG. 8 is a partial cross-sectional view of a generally planar, immobilizing blanket embodiment of the invention.

FIG. 9 is a cross-sectional isometric view of a wire rope embodiment of the invention.

FIG. 10 is a cross-sectional isometric view of an embodiment of the invention similar to that of FIG. 2 with a relatively loose container and strand binding straps.

DETAILED DESCRIPTION OF THE PREFERRED EMBODIMENTS

Turning now to FIGS. 1 and 2, immobilizing structure 2 is shown connected to a heating source 4. Heating source 4 includes a high capacity battery pack 6 connected to an electrical line 8 having a plug 10 at its outer end. Plug 10 mates with a receptacle 12 at one end 14 of structure 2. Structure 2 includes an elongate, flexible tubular container 16 housing flexible strands 18 extending along a substantial portion along the length of container 16 from an end cap 19 to receptacle 12. As shown in FIG. 2, strands 18 do not extend the complete length of tubular container 16 to allow for their relative longitudinal movement as structure 2 is bent or flexed.

Strands 18, in this preferred embodiment, are wound stainless steel music wire having a 1.22 mm diameter with a core diameter of 0.043 mm. Thus, as shown in FIG. 2A, the individual strands 18 have undulating or roughened surface character. Strands 18 are relatively tightly packed within tubular container 16 so that the surfaces of the adjacent strands 18 interlock. However, strands 18 are packed so that the strands 18 can move laterally small distances when structure 2 is bent or flexed. This allows strands 18 to slip past one another, thus allowing substantially free flexing of structure 2.

A thermoplastic material 20 is also contained within container 16 and surrounds or covers strands 18. Strands 18, although closely packed, are in effect embedded within thermoplastic material 20. Thermoplastic material 20, when melted or otherwise flowable, allows strands 18 to shift laterally the small amounts needed to allow the strands to move longitudinally relative to one another as immobilizing structure 2 is flexed. However, when thermoplastic material 20 is solid, it acts as a mechanical block to substantially inhibit or prevent strands 18 from shifting laterally. Thus, when thermoplastic material 20 is solid, strands 18 and material 20 becomes a rigid mass within container 16 thus preventing flexing and bending of structure 2.

Thermoplastic material 20 is, in this embodiment, a fusible alloy. It is essentially an eutectic alloy of lead, tin, bismuth and cadmium having a melting point of about 65° C. Under conventional ambient conditions thermoplastic material 20 will be a solid, thus locking structure 2 into a rigid form.

Structure 2 includes a flexible heating element 22 extending along substantially the entire length of tubular container 16. Heating element 22 is supplied electricity from heating source 4 upon connection of plug 10 to receptacle 12. Battery pack 6, typically a lead-acid automotive vehicle type of battery, supplies electricity through heating element 22 to heat thermoplastic material 20 and cause it to melt. The temperature of thermoplastic material 20 is monitored by a temperature gauge 24 at battery pack 6. Temperature gauge 24 is provided a signal from one or more positions within container 16 to a sensor socket 26 in receptacle 12. In use the user connects plug 10 to receptacle 12 to heat thermoplastic material 20 to a temperature sufficient to allow immobilizing structure 2 to flex. Although one could eliminate temperature gauge 24, having it allows the user to more closely control how long to heat thermoplastic material 20 and thus control how long immobilizing structure 2 remains flexible. If desired a thermostat may be used to regulate the temperature of thermoplastic material 20 to allow structure 2 to remain in a flexible, standby condition without operator intervention.

Turning now to FIG. 3, an alternative immobilizing structure 28 is shown. Structure 28 is similar to structure 2, but replaces receptacle 12 and end cap 19 by valve couplings 30. Valve couplings 30 each include a threaded end 32 for attachment to a source of heated or cooled fluid, not shown, and a handle 34 for controlling the flow of the fluid along a fluid conduit 36 extending centrally within container 16 between valve couplings 30. Using this arrangement, thermoplastic material 20 can be heated by passing a heated fluid, such as hot water, through conduit 36. Once in proper position, thermoplastic material can be quickly cooled by passing a cooled fluid, such as cold water, through conduit 36 thus minimizing the time it takes for thermoplastic material 20 to harden.

At FIG. 4 shows an alternative immobilizing structure embodiment 38 in which the tubular container 40 has a flattened or oval cross-sectional shape. Structure 38 lacks an internal heating element as do the embodiments of FIG. 1 and 3. Therefore, structure 38 is heated from an external source, such as by immersion in water or by blowing hot air over it using a heat gun. Other methods for heating thermoplastic material 20, such as by using induction or microwave energy, can be used as well.

Referring now to FIG. 5, immobilizing structure 2 can be wrapped around various body parts while thermoplastic material 20 is flowable, typically liquid. FIG. 5 shows structure 2 wrapped around a person's lower leg, ankle and foot. This is accomplished while thermoplastic material 20 is flowable. After immobilizing structure 2 cools sufficiently so that thermoplastic material 20 becomes solid, structure 2 becomes rigid thus forming a permanent or a temporary cast. Cooling time can be shortened by, for example, immersing structure 2 in a cold water bath, blowing cool air across it, or applying a cold pack to its outer surface.

FIG. 6 shows a further immobilizing structure embodiment 42 in the form of a blanket. Structure 2b includes a pair of tubular elements 44 woven into a transverse grid and sandwiched between and attached to sheets of material 46. Tubular elements 44 are similar to structure 28 of FIG. 3 but include common valve couplings 47. After heating, immobilizing blanket structure 42 can be wrapped around a person with possible neck or back injuries. After blanket structure 42 is in position, tubular elements 44 can be allowed to cool down slowly by natural convection; cooling can be hastened by passing a cold liquid through tubular elements 44. After thermoplastic material 20 solidifies, structure 42 is locked into shape.

FIG. 7 shows a second blanket immobilizing structure 48 similar to the blanket mobilizing structure 42 of FIG. 6. In this embodiment an immobilizing structure 2 of FIG. 1 is mounted between and attached to sheets of material 46 in a generally rectangular, spiral pattern. In both the embodiments of FIG. 6 and FIG. 7 the tubular elements are positioned so that no hinge lines, that is regions at which there is no substantial resistance to bending, exist. Other patterns of tubular elements can also be used.

FIG. 8 shows a further blanket immobilizing structure 52 which includes a sheet-like, planar container 54. Strands 18 are housed within container 54 in a transverse pattern. Container 54 remains essentially nonexpandable, thus keeping strands 18 closely spaced adjacent one another, through the use of numerous stays 56. Stays 56 are flexible, but very strong to be substantially non-stretchable in tension.

Referring to FIG. 9, a wire rope immobilizing structure 60 is shown. The elongate strands 18 of structure 60 are braided or woven into a flexible wire rope. Thermoplastic material 20 is interspersed between and among strands 18. A flexible container or cover 62 keeps thermoplastic material 20 from escaping when melted. However, the function of keeping strands 18 in close physical contact is performed primarily by the braided or woven configuration of strands 18 in structure 60, as opposed to container 16 of structure 2.

At FIG. 10 is illustrated a still further embodiment of immobilizing structure 64. Structure 64 is similar to that of FIGS. 1 and 2. However the function of keeping strands 18 against one another is accomplished by the use of binding straps 66 instead of by cover 16, which is relatively loose in structure 64. Thermoplastic material 20 is not shown in FIGS. 8, 9 and 10 for clarity.

The above described embodiments show how strands 18 can be maintained in the desirable generally parallel, closely grouped arrangements by the use of container 16 of structure 2, the braided or woven configuration of strands 18 of structure 60 and the binding straps 66 of structure 64. Strands 18 plus container 16, braided or woven strands 18, and strands 18 plus binding straps 66 are collectively denoted by the generic term strand ensembles. Strand ensembles shall include other groupings of generally parallel strands maintained in closely spaced, largely touching configurations either by virtue of some interlocking arrangement or by the use of some extraneous constricting or confining structure.

The invention has been described using strands 18 having roughened, often mechanically interlocking surfaces. Thus the resistance to relative longitudinal movement among strands 18 arises from the mechanical interlocking of the strand surfaces and also from any surface bonding which may be created between thermoplastic material 20 and strands 18. In some situations, depending in part upon the materials used for strands 18 and thermoplastic material 20, the strand surfaces may be relatively smooth so the rigidifying of the immobilizing structure would be created only by the surface bonding between the solid thermoplastic material and the strand surfaces. This may be sufficient, especially if strength is not a primary consideration.

Other modifications and variations can be made to disclosed embodiments without departing from the subject of the invention as defined in the following claims. For example, wires 18 can have their surfaces configured in a variety of shapes, contours and textures depending upon the particular applications and strength required. Also, it may be desired to mount one or more temperature gauges directly to container 16.

I claim:

1. A thermally actuated immobilizing structure comprising:
   a strand ensemble including elongate, generally parallel, closely grouped strands;
   a thermoplastic material interspersed among the strands, said strands and said themoplastic material adapted to permit relatively unhindered relative movement among the strands when said thermoplastic material is flowable and to substantially inhibit relative movement among the strands when said thermoplastic material is solid to lock the strands in place; and
   the strand ensemble including a flexible container housing the strands and thermoplastic material.

2. The structure of claim 1 wherein the container is sized to keep the strands closely grouped.

3. The structure of claim 1 wherein the strand ensemble includes binding straps which keep the strands closely grouped.

4. The structure of claim 1 wherein the strands of the strand ensemble are in a braided configuration which keeps the strands closely grouped.

5. The structure of claim 1 wherein said container is an elongate tube.

6. The structure of claim 5 wherein said tube has a circular cross-sectional shape.

7. The structure of claim 5 wherein said tube has a flattened cross-sectional shape.

8. The structure of claim 1 wherein said container is generally planar.

9. The structure of claim 8 wherein the elongate strands include a first set of parallel strands oriented transverse to a second set of parallel strands.

10. The structure of claim 9 wherein said first and second sets of strands are oriented perpendicular to one another.

11. The structure of claim 1 wherein the outer surfaces of said strands have surface configurations which interact to form a mechanical interlock when lying against one another.

12. The structure of claim 11 wherein said outer strand surfaces include spiral grooves.

13. The structure of claim 1 wherein said strands are wound metal music wire.

14. The structure of claim 1 wherein said thermoplastic material is metal.

15. The structure of claim 14 wherein said metal thermoplastic material is a lead, tin, bismuth, cadmium alloy with a melting point of about 65° C.

16. The structure of claim 1 further comprising a thermal energy transfer element thermally coupled to said thermoplastic material.

17. The structure of claim 16 wherein the thermal element is a heating element.

18. The structure of claim 17 further comprising an electrical receptacle electrically connected to said heating element.

19. The structure of claim 18 wherein said electrical receptacle is mounted to said container.

20. The structure of claim 16 wherein the thermal element is in physical contact with the thermoplastic material.

21. The structure of claim 16 further comprising thermometer means for indicating the temperature of the thermoplastic material.

22. The structure of claim 16 wherein the thermal element comprises a fluid conduit thermally coupled to said thermoplastic material for transferring heat between the thermoplastic material and a heat transfer fluid within the fluid conduit.

23. The structure of claim 22 further comprising a valve fluidly connected to the fluid conduit for controlling the flow of the heat transfer fluid in the fluid conduit.

24. The structure of claim 22 wherein the fluid conduit is positioned among the strands.

25. A thermally actuated immobilizing structure comprising:
   a strand ensemble including elongate, generally parallel strands and a flexible container housing said strands, the container sized to maintain the strands in a closely grouped arrangement, the strands having rough, interlocking surfaces to inhibit relative longitudinal movement between touching, parallel strands;
   a thermoplastic material distributed among the strands, the thermoplastic material and the strands adapted to permit relatively unhindered relative movement among the strands when the thermoplastic material is flowable and to substantially inhibit relative movement among the strands when the thermoplastic material is solid to lock the strands in position.

26. The structure of claim 25 further comprising means for heating the thermoplastic material.

27. A thermally actuated immobilizing structure comprising:
   a strand ensemble including elongate, generally parallel, closely grouped strands; and
   a thermoplastic material interspersed among the strands, said strands and said thermoplastic material adapted to permit relatively unhindered relative movement among the strands when said thermoplastic material is flowable and to substantially inhibit relative movement among the strands when said thermoplastic material is solid to lock the strands in place.

* * * * *